United States Patent
Dewey et al.

(10) Patent No.: US 6,939,876 B2
(45) Date of Patent: *Sep. 6, 2005

(54) PREVENTION OF ADDICTION IN PAIN MANAGEMENT

(75) Inventors: Stephen L. Dewey, Manorville, NY (US); Jonathan D. Brodie, Cos Cob, CT (US); Charles R. Ashby, Jr., Miller Place, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/124,660

(22) Filed: Apr. 18, 2002

(65) Prior Publication Data

US 2003/0004176 A1 Jan. 2, 2003

Related U.S. Application Data

(62) Division of application No. 09/853,548, filed on May 14, 2001, now abandoned.

(51) Int. Cl.[7] ........................ A61K 31/44; A61K 31/47; A61K 31/445; A61K 31/34; A61K 31/195

(52) U.S. Cl. ........................ 514/282; 514/310; 514/317; 514/327; 514/468; 514/561

(58) Field of Search ................................. 514/282, 310, 514/317, 327, 468, 561

(56) References Cited

U.S. PATENT DOCUMENTS 6,057,368 A * 5/2000 Dewey et al.
6,541,520 B1 * 4/2003 Dewey et al. .............. 514/561
6,593,367 B1 * 7/2003 Dewey et al. .............. 514/561

OTHER PUBLICATIONS

Astramorph in PDR, 50th Ed., 1996, 535–536.*

* cited by examiner

Primary Examiner—Shengjun Wang
(74) Attorney, Agent, or Firm—Margaret C. Bogosian

(57) ABSTRACT

The present invention provides a composition for treating pain. The composition includes a pharmaceutically acceptable analgesic and a GABAergic agent, such as gamma vinyl GABA, effective in reducing or eliminating the addictive liability of the analgesic. The invention also includes a method for reducing or eliminating the addictive

4 Claims, 1 Drawing Sheet

PREVENTION OF ADDICTION IN PAIN MANAGEMENT

This application is a divisional application of U.S. Ser. No. 09/853,584, filed May, 14, 2001, now abandoned.

This invention was made with Government support under contract number DE-AC02-98CH10886, awarded by the U.S. Department of Energy. The Government has certain rights in the invention.

BACKGROUND OF THE INVENTION

This invention relates to the prevention of addiction. More specifically, the invention relates to the administration of a compound to prevent addiction to analgesics often administered in pain management.

For many years, the treatment of postoperative pain and those conditions associated with chronic pain have been one of the most troubling and difficult areas of medicine. In general treatment has been so poor that laws have been enacted to ensure a patient's right to adequate pain management.

A major issue in pain management comes from the inability to quantify the adequacy of a pain control regimen. The clinical issues are complex, but it is clear that inadequate pain control leads to excessive morbidity and poor clinical outcomes.

It has long been known that exact pain control will improve the clinical outcome and be associated with little or no addiction liability. In a typical clinical situation, however, exact pain control is almost impossible to attain because pain generally fluctuates in intensity and rarely remains constant over time. On the other hand, treatment with opiates in excess of that required to control the pain often leads to chronic drug addiction and its unfortunate clinical and social consequences. See B. Meier and M. Petersen, "Medicine Merchants/Uses and Abuses: Use of Painkiller Grows Quickly. Along With Wide Spread Abuse," New York Times, Mar. 5, 2001 at Al.

In general, physicians have chosen to under treat pain because of their legitimate concern that the risk of generating a person who will be addicted to opiates long after the medical condition requiring opiate treatment had resolved.

Thus, there is a need to be able to administer effective, but addictive, analgesics without the unwanted side affect of developing an addiction to such analgesics.

SUMMARY OF THE PRESENT INVENTION

The present invention provides a composition for treating pain in a mammal. The composition includes a pharmaceutically acceptable analgesic having an addictive liability and a GABAergic agent effective in reducing or eliminating the addictive liability of the analgesic. In a preferred embodiment, the analgesic is a narcotic analgesic.

The GABAergic agent can be any agent that potentiates the GABAergic system or increased extra cellular and endogenous GABA levels in the central nervous system. Preferred GABAergic agents include Gamma vinyl GABA (GVG), gabapentin, valproic acid, progabide, gamma-hydroxybutyric acid, fengabine, cetylGABA, Topiramate, tiagabine and acamprosate (homo-calcium-acetyltaurine) The GABAergic agent can also include pharmaceutically acceptable salts of the GABAergic agent, an enantiomer or racemic mixture of the GABAergic agent, or any combinations of the forgoing. GVG is most preferred.

In a preferred embodiment, the addictive liability includes development of dependency or development of tolerance for the analgesic.

A method is also provided for reducing or eliminating the addictive liability of an analgesic in a host. The method includes administering an analgesic having an addictive liability to a host and also administering to said host a GABAergic agent effective in reducing or eliminating the addictive liability of the analgesic. It is preferred that the GABAergic agent be administered contemporaneously with the analgesic. The GABAergic agent can be administered before, after, or simultaneously, with the analgesic, or any combination thereof. In a preferred embodiment, the analgesic and GABAergic agent are administered simultaneously in a single composition.

In a separate preferred embodiment, the reduction or elimination of the addictive liability of the analgesic occurs in the absence of an aversive or appetitive response to the GABAergic agent. In a separate preferred embodiment, the reduction or elimination of the addictive liability is measured by conditioned place preference (CPP).

The analgesic can be any analgesic. An analgesic with an addictive liability. for example, a narcotic analgesic, is preferred. Examples of narcotic analgesics include alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone. hydromorphone, hydroxypethidine, isomethadone, ketobemidone, levallorphan, levorphanol, levophenacylmorphan, lofentanil, meperidine, meptazinol, metazocine, methadone. metopon. morphine, myrophine, nalbuphine. narceine, nicomorphine, norlevorphanol, normethadone, nalorphine, normorphine, norpipanone, opium, oxycodone, OxyContin®, oxymorphone, papaveretum, pentazocine, phenadoxone, phenomorphan, phenazocine, phenoperidine, piminodine, piritramide, proheptazine, promedol, properidine, propiram, propoxyphene, sufentanil, tramadol, tilidine, salts thereof, mixtures of any of the foregoing, mixed mu-agonists/antagonists, mu-antagonist combinations.

Preferred GABAergic agents include Gamma vinyl GABA (GVG), gabapentin, valproic acid, progabide, gamma-hydroxybutyric acid, fengabine, cetylGABA, topiramate, tiagabine, acamprosate (homo-calcium-acetyltaurine), pharmaceutically acceptable salts thereof, enantiomers or a racemic mixture thereof, or any combinations thereof. GVG is most preferred.

In the method of the invention, the host will generally be mammalian. A human host is most preferred.

The preferred amounts of GABAergic agents will vary. For example, in humans, it is preferred that GVG be administered in an amount of about 500 mg/day to about 6 g/day. It is preferred that gabapentin be administered to humans in an amount of about 600 mg/day to about 3600 mg/day. It is preferred that valproic acid be administered to humans in an amount of about 500 mg/day to about 2500 mg/day. It is preferred that topiramate be administered to humans in an amount of about 100 mg/day to about 1000 mg/day. It is preferred that progabide be administered to humans in an amount of about 1000 mg/day to about 3000 mg/day. It is preferred that fengabine be administered to humans in an amount of about 700 mg/day to about 4000 mg/day It is preferred that gamma-hydroxybutyric acid be administered in an amount of about 1000 mg/day to about 5000 mg/day.

The composition of the invention reduces or eliminates the addictive liability of analgesics without interfering with the therapeutic analgesic effects. This activity of the composition has the consequence of increasing the therapeutic index of the analgesic agent by reducing or eliminating addiction as a major source of post treatment morbidity. Thus, the composition enables full and continuing pain control with less concern for generating post treatment drug addicts and abusers.

DETAILED DESCRIPTION OF THE INVENTION

Figure 1:
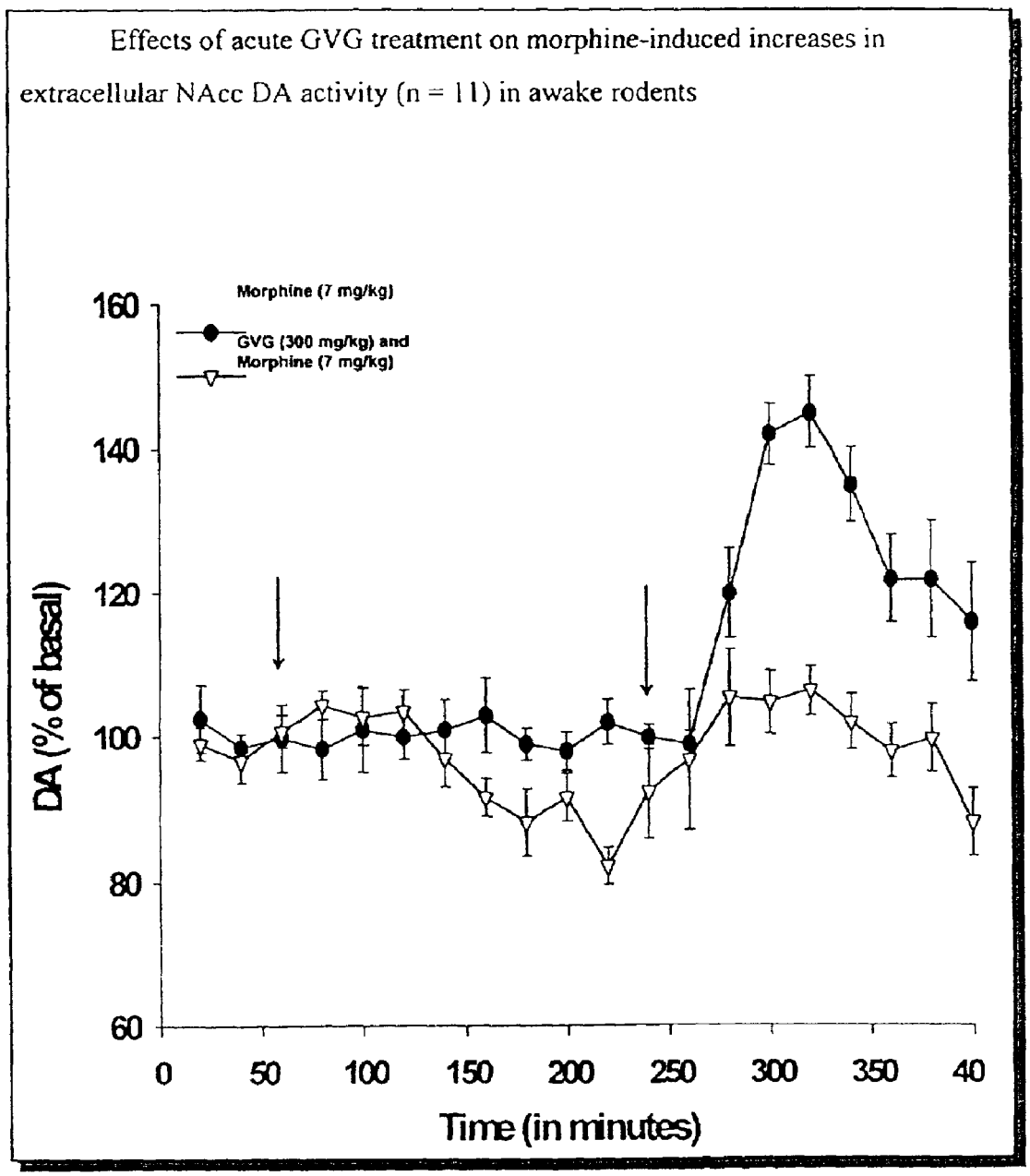
FIG. 1 is a graph illustrating the effect of GVG on morphine-induced DA release in the nucleus accumbens (NAcc).

The composition of the invention includes an analgesic compound suitable for use in reducing pain and a GABAergic agent effective in reducing or eliminating the addictive liability of the analgesic. By administering the compounds together in one composition, the composition of the invention reduces or eliminates the addictive liability of the compound administered to treat pain.

Analgesics are very often administered in the treatment of post operative pain, both surgical and orthopedic. This pain is usually characterized by fluctuating but gradually diminishing intensity over a period of days to weeks and months and requires ongoing pain management. Analgesics are also often utilized in the treatment of chronic pain conditions, such as chronic back pain and sciatica and other neuralgias The analgesic compound can be any pharmaceutically acceptable analgesic for the treatment of pain, as is known in the art. Combinations of analgesics can also be used. However, the benefits of the compound are most realized when the analgesic agent possesses an addictive liability.

Analgesics that possess an addictive liability are defined herein as those analgesics that are recognized to develop physical and/or psychological dependency following a single administration or repeated administrations for a short or prolonged period of time, and/or substantially develop tolerance to analgesic action thereof by repeated administrations for a short or prolonged period of time.

Examples of such analgesics include narcotic analgesics. Narcotic analgesics are conventionally used in treating pain. Narcotic analgesics include, for example, opioid analgesics such as alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofenitanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone. OxyContin®, oxymorphone, papaveretum, pentazocine, phenadoxone, phenomorphan, phenazocine, phenoperidine, piminodine, piritramide, propheptazine, promedol, properidine, propiram, propoxyphene sufentanil, tramadol, tilidine, salts thereof, mixtures of any of the foregoing, mixed mu-agonists/antagonists, mu-antagonist combinations, and the like.

Examples also include analgesic peptides as endogenous morphine-like substances such as, for example, enkephalins such as methionine enkephalin and leucine enkephalin; endorphins such as alpha-endorphin, beta-endorphin, and gamma-endorphin; and dynorphins such as dynorphin A and dynorphin B, and precursors thereof whose examples include proenkephalins such as proenkephalins, propiomelanocortins, and prodynorphins.

The analgesics are not limited to any physical form. The analgesic can be, for example, a solid or liquid. Two examples of liquid form analgesics are codeine syrups and Brompton's cocktail.

The composition of the present invention can further include one or more additional drugs which may or may not act synergistically with the analgesics utilized in the present invention. Examples of such additional drugs include non-steroidal anti-inflammatory agents, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid tolfenamic acid, diflurisal, flufenisal, piroxicam, sudoxicam or isoxicam, and the like. Other suitable additional drugs which may be included in the dosage forms of the present invention include acetaminophen, aspirin, and other non-opioid analgesics.

GABAergic agents as defined herein are agents that potentiate the GABAergic system or increase extracellular endogenous GABA levels in the central nervous system (CNS). Such compositions or medicaments include agents that enhance the production Or release of GABA in the CNS. As used herein, enhancing or increasing endogenous CNS GABA levels is defined as increasing or up-regulating GABA levels substantially over normal levels in vivo, within a mammal. Preferably, endogenous CNS GABA levels are enhanced at least by from about 10% to about 1000% over normal levels.

GABAergic agents include, but are not limited to, Gamma vinyl GABA (GVG), gabapentin, valproic acid, progabide, gamma-hydroxybutyric acid, fengabine, cetylGABA, Topiramate, tiagabine, and acamprosate (homo-calcium-acetyltaurine). The GABAergic agents can also include pharmaceutically acceptable salts of the GABAergic agent and enantiomer or a racemic mixtures of the GABAergic agent, or any combinations of the foregoing.

Different enantiomers may be synthesized from chiral starting materials, or the racemates may be resolved by conventional procedures which are well known in the art of chemistry; such as chiral chromatography, fractional crystallization of diastereomeric salts, and the like.

Gabapentin is available as Neurontin® from Parke-Davis in the United States. Valproic acid is available as Depakene® and Depakote® from Abbott in the United States. Progabide is available as Gabrene® from Synthelabo, France. The chemical formula of progabide is $C_{17}H_{16}N_2O_2$. Fengabine is available as SL 79229 from Synthelabo, France. The chemical formula of fengabine is $C_{17}H_{17}C_{12}NO$. Gamma-hydroxybutyric acid is available from Sigma Chemical. The chemical formula of gamma-hydroxybutyric acid is $C_4$ $H_7O_3$ Na. Topiramate is a sulfamate-substituted monosaccharide of the formula $C_{12}H_{21}NO_8S$ and is available commercially as Topomax® from McNeil in the United States.

GABAergic agents also embrace compositions or medicaments which include prodrugs of GABA or drugs which contain GABA as a moiety in its chemical structure The prodrugs become pharmacologically active when metabolically, enzymatically or non-enzymatically biotransformed or cleaved into GABA in the CNS. An example of a prodrug of GABA is progabide which, upon crossing the blood brain barrier, increases endogenous CNS GABA levels.

Gamma vinyl GABA (GVG) is a selective and irreversible inhibitor of GABA-transaminase (GABA-T) known to potentiate GABAergic inhibition. GVG is $C_6H_{11}NO_2$ or 4-amino-5-hexanoic acid available as VIGABATRIN® from Hoechst Marion Roussel. GVG does not bind to any receptor or reuptake complex, but increases endogenous intracellular GABA levels by selectively and irreversibly inhibiting GABA-transaminase (GABA-T), the enzyme that normally catabolizes GABA.

As used herein GVG includes the racemic compound or mixture which contains equal amounts of S(−)-gamma-vinyl GABA, and R(−)-gamma vinyl GABA. This racemic compound of GVG is available as SABRIL® from Aventis Pharma AG.

GVG contains asymmetric carbon atoms and thus is capable of existing as enantiomers. The present invention embraces any enantiomeric form of GVG including the racemates or racemic mixture of GVG. In some cases there may be advantages, i.e. greater efficacy, to using a particular enantiomer when compared to the other enantiomer or the racemate or racemic mixture in the methods of the instant invention and such advantages can be readily determined by those skilled in the art. For example, the enantiomer S(+)-gamma-vinyl GABA is more effective at increasing endogenous intracellular GABA levels than the enantiomer R(−)-gamma-vinyl GABA.

As used herein, pharmaceutically acceptable salts include those salt-forming acids and bases which do not substantially increase the toxicity of the compound. Some examples of suitable salts include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g. p-toluenesulfonic acids, and the like.

All modes of administration are contemplated for the composition of this invention. Systemic modes of administration, such as oral and parenteral are preferred. The administration of the composition of the invention can also include controlled-release delivery systems, as is known in the art.

The composition will ordinarily be formulated with one or more pharmaceutically acceptable ingredients in accordance with known and established practice. Thus, the composition can be formulated, for example, as a liquid, powder, elixir, injectable solution or suspension, etc. Formulations for oral use can be provided as tablets, caplets or hard capsules wherein the pharmacologically active ingredients are mixed with an inert solid diluent such as calcium carbonate, calcium phosphate or kaolin, or as soft gelatin capsules wherein the active ingredients are mixed with an oleaginous medium, e.g., liquid paraffin or olive oil.

Examples of the pharmaceutical compositions suitable for parenteral administration include, for example, injections for subcutaneous, intravenous, and intramuscular injections, drip infusions, suppositories, inhalants, transdermal preparations, transmucosal preparations, and patches. Examples of the pharmacologically and pharmaceutically acceptable additives include, for example, excipients, disintegrators or disintegrating aids, binders, lubricants, coating agents, coloring agents, diluents, base materials, solubilizers or solubilizing aids, isotonicities, pH modifiers, stabilizers, propellants, and adhesives.

Aqueous suspensions can include pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g, heptadecaethyleneoxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides. e.g., polyoxyethylene sorbitan monoleate. The aqueous suspensions can also contain one or more preservatives. e.g., ethyl-or-n-propyl-p-hydroxy benzoate, one or more coloring agents, one or more flavoring agents and one or more sweetening agents, such as sucrose, saccharin or sodium or calcium cyclamate.

For intranasal administration, the compounds of the invention can be used, for example, as a liquid spray, as a powder or in the form of drops. For administration by inhalation, the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit can be determined by providing a valve to deliver a metered amount. Capsules and cartridges of, for example, gelatin, for use in an inhaler or insulator can be formulated containing a powder mix of a compound of the invention and a suitable powder base such as lactose or starch.

The dose of the analgesic is that amount effective to prevent occurrence of the symptoms of pain or to treat some symptoms of pain from which the host suffers, as is known in the art. The amount of the analgesic in the composition may suitably be chosen depending on, for example, administration route, degree of the development of dependency and/or the development of tolerance, purpose of administration such as prophylactic or therapeutic administration, and the age or body weight of a patient. Also, because the composition of the invention is effective in inhibiting or eliminating the addictive liability of the analgesic, higher doses of the analgesic may be administered to the host.

By "effective amount" of analgesic, it is meant that amount sufficient to elicit the desired pharmacological or therapeutic effects, thus resulting in effective prevention or treatment of pain. Prevention of pain is manifested by prolonging or delaying the onset of pain. Treatment of pain is manifested by a reduction in the symptoms of pain associated with pain or amelioration of the re-occurrence of the symptoms of pain. The specific amount of analgesic in the composition of the invention will vary depending upon, among other things, the individual to be treated, the source and severity of the pain, and the specific type of analgesic administered, as is known in the art. In humans, for example, an effective amount can vary from about 5 $\mu$g to about 1000 mg. preferably from about 50 $\mu$g to about 100 mg.

The amount of GABAergic agent in the composition of the invention is that amount effective in reducing or eliminating the addictive liability of the analgesic. It is preferred that the GABAergic agent also be administered in an amount that minimizes any potential side effects in the host. The effective amount will vary depending upon the dose of analgesic administered. The amount of GABAergic agent can vary due to additional factors, for example, on administration route, the addictive liability of the analgesic, the tolerance of the host to the analgesic, and age or body weight. In a preferred embodiment, the GABAergic agent will also have little or no effect on the therapeutic effects of the analgesic. In humans, for example, the preferred amount of GABAergic agent in the composition is about 0.5 to about 5 grams.

As to examples of the dose, where the composition of the invention includes a narcotic analgesic agent, such as morphine hydrochloride or morphine nitrate, in an amount from about 10 to 30 mg, the composition of the invention can typically include between about 25 to about 1000 mg, preferably from about 100 to about 500 mg of GABAergic agent, such as GVG.

The host or patient for the analgesic therapeutic treatment using the analgesic compounds described herein generally is mammalian. Mammals include, for example, humans, baboons and other primates, as well as pet animals such as dogs and cats, laboratory animals such as rats and mice, and farm animals such as horses, sheep, and cows.

Without being bound by theory, it is believed that the addictive liability of narcotic analgesics is linked to its pharmacological actions on mesotelencephalic dopamine (DA) reinforcement/reward pathways in the central nervous system (CNS). Dopaminergic transmission within these pathways is modulated by gamma-amino butyric acid (GABA).

It has been found that addicting drugs such as morphine and other analgesic drugs used in the treatment of pain enhance dopamine (DA) within the mesotelencephalic reward/reinforcement circuitry of the forebrain, producing the enhanced brain reward that constitutes the drug user's "high." Alterations in the functions of the dopamine (DA) systems have also been implicated in drug craving and in relapse to the drug-taking habit in recovering addicts. For example, morphine acts on these DA systems by binding to the dopamine transporter (DAT) and preventing DA reuptake into the presynaptic terminal. There is considerable evidence that the addictive liability of addicting drugs is linked to the reuptake blockade in central nervous system (CNS) reward/reinforcement pathways.

It is believed that narcotic analgesics inhibit the presynaptic reuptake of monoamines. Dopaminergic neurons of the mesocorticolimbic DA system, whose cell bodies lie within the ventral tegmental area (VTA) and project primarily to the nucleus accumbens (NAcc), appear to be involved in narcotic reinforcement. Electrical stimulation of reward centers within the VERA increases extracellular DA levels in the NAcc, while 6-hydroxy dopamine lesions of the NAcc abolish self-administration of addicting drugs. In vivo microdialysis studies confirm morphine's ability to increase extracellular DA in the NAcc.

γ-Amino butyric acid (GABA)ergic neurons in the NAcc and ventral pallidum project onto DA neurons in the VTA. Pharmacologic and electrophysiologic studies indicate these projections are inhibitory. Inhibition of VTA-DA neurons is likely the result of $GABA_B$ receptor stimulation. In addition, microinjection of baclofen into the VTA, acting via these receptor subtypes, can decrease DA concentrations in the NAcc. Taken together, it is evident that pharmacologic manipulation of GABA may effect DA levels in the NAcc through modulation of VTA-DA neurons.

Based on the knowledge that narcotic analgesics increase extracellular NAcc DA and the fact that GABA inhibits DA in the same nuclei, the inventors have shown that GABAergic agents can attenuate narcotic analgesic-induced changes in extracellular DA. For example, GVG significantly attenuated morphine-induced DA increases in the nucleus accumbens in rats (NAcc). See Example 1.

Therefore, the inventors have developed the utility of a pharmacologic strategy targeted at the GABAergic neurotransmitter system, a system distinct from but functionally linked to the DA mesotelencephalic reward/reinforcement system. In avoiding the addictive liability in administering analgesics for treatment of pain However, rather than targeting the GABA receptor complex with a direct GABA agonist, this novel approach with GABAergic agents takes advantage of the prolonged effects of an irreversible enzyme inhibitor that raises endogenous GABA levels without the addictive liability, associated with GABA agonists acting directly at the receptor itself Thus, the GABAergic agent can eliminate the addiction liability of the analgesic by interfering with the process that produces craving and reward without interfering with the ability of the analgesic to reduce pain in the host.

Accordingly, a method is provided for reducing or eliminating the addictive liability of an analgesic as defined above in a host. The method includes administering the analgesic to the host and administering an effective amount of a GABAergic agent.

As discussed above, the analgesic can be any pharmaceutically acceptable analgesic for the treatment of pain, as is known in the art, including combinations of analgesics. In a preferred embodiment, the analgesics possess an addictive liability. The analgesics also are not limited to any physical form. The analgesic can be, for example, a solid or liquid. Two examples of liquid form analgesics are codeine syrups and Brompton's cocktail.

As discussed above, analgesics that possess an addictive liability are defined herein as those analgesics that are recognized to develop dependency characteristics by a single administration or repeated administrations for a short or prolonged period of time, and/or substantially develop tolerance to analgesic action thereof by repeated administrations for a short or prolonged period of time.

An effective amount of GABAergic agent, as defined herein, is that amount effective in reducing or eliminating the addictive liability of the analgesic. It is preferred that the GABAergic agent also be administered in an amount that minimizes any potential side effects in the host. The effective amount will vary depending upon the dose of analgesic administered. The amount of GABAergic agent can vary due to additional factors, for example, the administration route, the addictive liability of the analgesic, the tolerance of the host to the analgesic, and age or body weight. In a preferred embodiment, the GABAergic agent will also have little or no effect on the therapeutic effects of the analgesic.

The effective amount of GABAergic agent should be sufficient to increase endogenous CNS GABA levels. As used herein, increasing endogenous CNS GABA levels is defined as increasing or up-regulating GABA levels substantially over normal levels in vivo, within a mammal. Preferably, endogenous CNS GABA levels are enhanced at least by from about 10% to about 1000% over normal levels.

Examples of an effective amount of GVG in mammals include an amount from about 10 mg/kg/day to about 100 mg/kg/day, preferably from about 25 mg/kg/day to about 80 mg/kg/day. In humans, the preferred range is from about 500 mg/day to about 6 g/day, more preferably from 1 g/day to 4 g/day.

Examples of an effective amount of gabapentin in mammals include an amount from about 10 mg/kg/day to about 40 mg/kg/day, preferably from about 15 mg/kg/day to about 30 mg,/kg/day. In humans, the preferred range is from about 600 mg/day to about 3600 mg/day, more preferably from 900 mg/day to 2400 mg/day. Gabapentin is available as NEURONTIN® from Parke-Davis in the United States.

Examples of an effective amount of valproic acid in mammals include an amount from about 10 mg/kg/day to about 60 mg/kg/day, preferably from about 15 mg/kg/day to about 30 mg/kg/day. In humans, the preferred range is from about 500 mg/day to about 2500 mg/day, more preferably from 750 mg/day to 1750 mg/day Valproic acid is available as DEPAKENE® and DEPAKOTE® of from Abbott in the United States.

Examples of an effective amount of topiramate in mammals include an amount from about 5 mg/kg/day to about 80 mg/kg/day, preferably from 5 mg/kg/day to about 15 mg/kg/day. In humans, the preferred range is from about 100 mg/day to about 1000 mg/day, more preferably from 200 mg/day to 600 mg/day. Topiramate is available as TOPAMAX® from McNeil in the United States.

Examples of an effective amount of progabide in mammals include an amount from about 5 mg/kg/day to about 75 mg/kg/day, preferably from 15 mg/kg/day to about 45 mg/kg/day. In humans, the preferred range is from about 1000 mg/day to about 3000 mg/day, more preferably from 1500 mg/day to 2500 mg/day. Progabide is available as GABRENE® from Synthelabo, France. The chemical formula of progabide is $C_{17} H16 N_2O_2$.

Examples of an effective amount of fengabine in mammals include an amount from about 5 mg/kg/day to about 80 mg/kg/day, preferably from 15 mg/kg/day to about 50 mg/kg/day. In humans, the preferred range is from about 700 mg/day to about 4000 mg/day, more preferably from 1000 mg/day to 3000 mg/day. Fengabine is available as SL 79229 from Synthelabo, France. The chemical formula of fengabine is $C_{17} H_{17} C_{12} NO$.

Examples of an effective amount of gamma-hydroxybutyric acid in mammals include an amount from about 5 mg/kg/day to about 100 mg/kg/day, preferably from 10 mg/kg/day to about 80 mg/kg/day. In humans, the preferred range is from about 700 mg/day to about 5000 mg/day, more preferably from 1000 mg/day to 4000 mg/day. Gamma-hydroxybutyric acid as the sodium salt is available from Sigma Chemical.

Compulsive drug use includes three independent components: tolerance, psychological dependence, and physical dependence. Tolerance produces a need to increase the dose of the drug after it is used several times in order to achieve the same magnitude of effect. Physical dependence is an adaptive state produced by repeated drug administration and which manifests itself by intense physical disturbance when drug administration is halted. Psychological dependence is a condition characterized by an intense drive, craving or use for a drug whose effects the user feels are necessary for a sense of well being. See Feldman, R. S. and Quenzer, L. F. "Fundamentals of Neuropsychopharmocology" 418–422 (Sinaur Associates, Inc.) (1984) incorporated herein by reference as if set forth in full. Based on the foregoing definitions, as used herein "dependency characteristics" include all characteristics associated with compulsive drug use, characteristics that can be affected by biochemical composition of the host, physical and psychological properties of the host.

Rewarding/incentive effects refers to any analgesic stimulus that produces anhedonia or increases the probability of a learned response. This is synonymous with reinforcement. With respect to experimental animals, a stimulus is deemed to be rewarding by using paradigms that are believed to measure reward. This can be accomplished by measuring whether stimuli produce an approach response, also known as an appetitive response or a withdrawal response, as when the animal avoids the stimuli, also known as an aversive response. Conditioned place preference (CPP) is a paradigm which measures approach (appetitive) or withdrawal (aversive) responses. One can infer that rewarding stimuli produce approach behavior. In fact, one definition of reward is any stimulus that elicits approach behavior. Furthermore, the consequences of reward would be to enhance the incentive properties of stimuli associated with the reward.

Reward can also be measured by determining whether the delivery of a reward is contingent upon a particular response, thereby increasing the probability that the response will reappear in a similar situation. i.e. reinforcement paradigm. For example, a rat pressing a bar a certain number of times for an injection of a drug is an example of reinforcement. Yet another way to measure reward is by determining if a stimulus (e.g. a drug), through multiple pairings with neutral environmental stimuli, can cause the previously neutral environmental stimuli to elicit behavioral effects initially only associated with the drug. This is conditioned reinforcement. CPP is considered to be a form of conditioned reinforcement.

The incentive motivational value of a drug can be assessed using conditioned place preference (CPP). Animals are tested in a drug-free state to determine whether they prefer an environment in which they previously received the drug as compared to an environment in which they previously received saline. In the CPP paradigm, animals are given the drug in one distinct environment and are given the appropriate vehicle in an alternative environment. The CPP paradigm is widely used to evaluate the incentive motivational effects of drugs in laboratory animals. After conditioning or pairing with the drug, if the animal, in a drug-free state, consistently chooses, the environment previously associated with the drug, the inference is drawn that the appetitive value of the drug was encoded in the brain and is accessible in the drug-free state. CPP is reflected in an increased duration spent in the presence of the drug-associated stimuli relative to vehicle-injected control animals.

It has been postulated that since craving at the human level is often elicited by sensory stimuli previously associated with drug-taking, conditioning paradigms like CPP may be used to model craving in laboratory animals.

As used herein, craving an analgesic is a desire to self-administer the analgesic previously used by the mammal. The mammal does not necessarily need the analgesic to prevent withdrawal symptoms.

As discussed above, any form of administration is contemplated in the method of the invention. The GABAergic agent can be administered before, during, or simultaneous with the analgesic, or any combination thereof. Simultaneous administration is preferred. If the administration of GABAergic agent and analgesic is simultaneous, the composition of the invention as described above can be utilized.

Systemic administration by the parenteral and enteral routes is preferred. For example, the GABAergic agents can be administered intravenously, or intraperitoneal (i.p.).

Oral or enteral use in also contemplated. Formulations such as tablets, capsules. pills, troches, elixirs, suspensions, syrups, wafers, chewing gum and the like can be employed to provide the GABAergic agent.

The following examples are provided to assist in a further understanding of the invention. The particular materials and conditions employed are intended to be further illustrative of the invention and are not limiting upon the reasonable scope thereof.

EXAMPLE 1

The effects of increased endogenous GABA activity on morphine-induced extracellular DA concentrations in the nucleus accumbens (NAcc) of freely moving rats was explored.

All animals there used under an IACUC-approved protocol and with strict adherence to the NIH guidelines. Adult male Sprague-Dawley rats (200–300 g, Taconic Farms), housed in the animals care facility under 12:12 light/dark conditions, were placed into 6 groups (n=3–6), anesthetized and siliconized guide cannulae were stereotactically implanted into the right NAcc (2.0 mm anterior and 1.0 mm lateral to bregms, and 7.0 mm ventral to the cortical surface) and prefrontal cortex (PFC) at least 4 days prior to study. Microdialysis probes (2.0 mm, Bioanalytical Systems, BAS, West Lafayette. Ind.) were positioned within the guide cannulae and artificial cerebrospinal fluid (ACSF. 155.0 mM NA⁻, 1.1 mM Ca²⁻, 2.9 mM K⁻, 132.76 mM Cl⁻, and 0.83 mM Mg²⁻) was administered through the probe using a CMA/100 microinfusion pump (BAS) at a flow rate of 2.0 µl/min.

Animals were placed in bowls, and probes were inserted and flushed with ACSF overnight. On the day of the study. a minimum of three samples were injected to determine baseline stability. Samples were collected for 20 min. and injected on-line (CMA/160, BAS). The average dopamine concentration of these three stable samples was defined as control (100%). and all subsequent treatment values were transformed to a percentage of that control. Upon establishing a stable baseline, the morphine was administered by intraperitoneal (i.p.) injection. The high performance liquid chromatography (HPLC) system consists of a BAS reverse-phase column (3.0 µC-18), a BAS LC-4C electrochemical transducer with a dual/glassy carbon electrode set at 650 mV, a computer that analyzes data on-line using a commercial software package (Chromograph Bioanalytical Systems), and a dual pen chart recorder. The mobile phase (flow rate 1.0 ml/min) consisted of 7.0% methanol, 50 mM sodium phosphate monobasic, 1.0 mM sodium octyl sulfate, and 0.1 mm EDNA, pH 4.0. DA eluted at 7.5 min.

Gamma-vinyl GABA (GVG), an irreversible inhibitor of GABA-transaminase, was administered by intraperitoneal injection 2.5 hours prior to morphine (7 mg/kg). In all studies, animals were placed in the microdialysis bowls the night before the experiment and artificial cerebrospinal fluid (ACSF) was perfused through the microdialysis probes at a flow rate of 2.0 µl/min. At the end of each study, animals were sacrificed and their brains were removed and sectioned for probe placement verification Levels of extracellular DA were sampled from the NAcc continuously using a stereoaxically implanted probe. The results are shown in FIG. 2. Morphine alone increases DA concentrations 50% above baseline in the NAcc ($p<0.01$, T=3.79). GVG dose dependently diminished the DA response to morphine in the NAcc, with no significant inhibition after 150 mg/kg, 62% attenuation following 300 mg/kg ($p<0.01$. T=4.97) and 67% attenuation following 500 mg/kg ($p<0.001$, T=6.02). This data indicates the GABAergic system as a target for reducing or eliminating analgesic addictive liability by reducing extracellular DA concentrations.

EXAMPLE 2

The effect of GVG on the analgesic potency of morphine in male Sprague-Dawley rats was examined using the hot plate test. In this paradigm, animals are treated and placed on a hot plate at a temperature of 53 degrees Centigrade and the latency to licking of one of the forepaws was measured. This test is used as screen for agents that have moderate to significant analgesic action as these drugs will increase latency to forepaw licking.

The rats were treated with either vehicle or GVG 2.5 hours prior to receiving either vehicle or morphine. Animals were given either vehicle or morphine 30 minutes prior to placing them on a hot plate at a constant temperature of 53 degrees Centigrade. Analgesic potency was assessed by measuring the latency to forepaw licking after placement on the hot plate. A total of 10 rats were examined for each treatment group. Each value represents the latency in seconds to forepaw licking +S.E.M. The results are set forth in Table 1.

TABLE 1

| Pretreatment | Treatment | Licking latency (sec) |
|---|---|---|
| Vehicle, 1 ml/kg | Vehicle, 1 ml/kg | 11 ± 0.8 |
| GVG, 300 mg/kg | Vehicle, 1 ml/kg | 17 ± 1.4+ |
| Vehicle, 1 ml/kg | Morphine, 10 mg/kg | 27 ± 3.0* |
| GVG, 300 mg/kg | Morphine, 10 mg/kg | 27 ± 2.9# |

*Significantly greater than Vehicle pretreatment/Vehicle treatment, $p < 0.01$, ANOVA and Student-Newman-Keuls test.
Significantly greater than GVG pretreatment/Vehicle treatment, $p < 0.05$, ANOVA and Student-Newman-Keuls test
+Significantly greater than Vehicle pretreatment/Vehicle treatment, $p < 0.05$, ANOVA and Student-Newman-Keuls test The results clearly indicate that 10 mg/kg i.p. of morphine produces a significant increase in the latency to forepaw licking compared to vehicle-treated animals, i.e. morphine produces an analgesic effect. In addition, GVG+vehicle produced a significantly greater latency than vehicle+vehicle. However, the administration of GVG 2.5 hrs prior to morphine did not significantly alter the latency to forepaw licking compared to vehicle+morphine. These results indicate that 300 mg/kg i.p of GVG, does not alter the analgesic potency of morphine.

EXAMPLE 3

Heroin-induced conditioned place preference was then examined. Heroin is an effective analgesic, similar to morphine.

In all rodent studies, male Sprague-Dawley rats were used (200–225 g. Taconic farms, Germantown, N.Y.). Animals were allowed to acclimate to the animal housing facility for at least 5 days prior to beginning the experiments. Conditioned place preference (CPP) chambers were used as previously described (Lepore et al., 1995), except instead of one chamber being entirely white and the other black, one chamber was entirely light blue with a stainless steel floor and the second chamber was light blue with horizontal black stripes (2.5 cm wide) spaced 3.8 cm apart with a smooth plexiglass floor. In all CPP studies with GVG, the saline volume was (1 ml/kg), and the heroin doses were 1.5 mg/kg. The saline, heroin and GVG were all injected intraperitonealy (i.p.). The conditioning procedure for the acquisition phase consisted of 12 sessions carried out consecutively over 12 days.

The CPP pairings were: 1) saline/saline 2) saline/heroin 3) GVG/saline 4) saline/heroin and GVG. The animals in each group were randomly assigned to a 2×2 factorial design ,with one factor being the pairing chamber and the other factor being the order of conditioning. The animals that received either saline or heroin were injected and confined to the appropriate compartment for 30 minutes. The GVG injections were given 3 hours before saline or heroin injection and subsequent placement of the animals in the appropriate chamber. This was done as it has been shown that GABA levels reach maximal values 3 to 4 hours following GVG administration.

On the test day (day 12), neither drugs nor saline were administered and the animal was allowed to move freely between both chambers for fifteen minutes. The amount of time spent in each chamber was recorded using an automated infrared beam electronically coupled to a timer. For the expression phase of CPP to heroin, the animals were habituated and conditioned to heroin as described in the acquisition studies, but no animals in the expression studies were given GVG on conditioning days. On the test day (day 12), the animals being tested in the expression phase, unlike the animals in the acquisition phase, received either saline or GVG 2.5 hours before they were placed in the apparatus and allowed free access to both chambers for 15 minutes.

The results are set forth in Table 2 below.

TABLE 2

| Treatment Pairings Paired/Unpaired | Drug given on test day | Time spent in chambers (min) Paired | Unpaired |
|---|---|---|---|
| Vehicle/Vehicle | Vehicle[2] | 7.4 ± 0.4[1] | 7.6 ± 0.4 |
| Vehicle/Heroin | Vehicle | 10.9 ± 0.4* | 4.1 ± 0.4# |
| Vehicle/Heroin | GVG. 300 mg/kg | 6.6 ± 0.7 | 8.4 ± 0.7 |
| Vehicle/Vehicle | GVG. 300 mg/kg | 7.4 ± 0.3 | 7.6 ± 0.3 |

[1]Each value represents the mean number of minutes spent in each chamber ± S E M Eight to ten rats were examined for each treatment pairing.
[2]The vehicle was 1 ml/kg i.p. of 0.9% saline
*Significantly greater than all other groups, $p < 0.01$, ANOVA and Student-Newman-Keuls test
Significantly less than all other groups, $p < 0.01$, ANOVA and Student-Newman-Keuls test The results clearly indicated that 300 mg/kg of GVG blocked the expression of heroin-induced CPP.

Therefore, the results of Table 1 and Table 2 taken together demonstrated that GVG was able to block the craving for heroin, a powerfully addictive analgesic, while not decreasing analgesic effectiveness on reducing pain. Thus, a GABAergic agent, such as GVG used in combination with opioid analgesics will decrease the likelihood of addiction to the analgesic without decreasing their therapeutic effects in pain management.

While there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A method for treating pain in a host with an opioid analgesic having addictive liability while decreasing the host's likelihood of addiction to said opioid analgesic comprising:
   i. administering to said host an effective amount of an opioid analgesic; and
   ii. administering to said host an effective amount of gamma vinyl GABA;
   wherein said gamma vinyl GABA is administered before or simultaneously with said analgesic.

2. A method as described in claim 1, wherein said opioid analgesic is morphine.

3. A method as described in claim 1, wherein said analgesic and said gamma vinyl GABA are administered in a single composition.

4. A method as described in claim 1, wherein the gamma vinyl GABA is administered in an amount of about 500 mg/day to about 6 g/day.

* * * * *